United States Patent [19]

Fried

[11] Patent Number: 5,166,408
[45] Date of Patent: Nov. 24, 1992

[54] PREPARATION OF CARBOXYLIC ACID ESTERS

[75] Inventor: Herbert E. Fried, Houston, Tex.

[73] Assignee: Shell Oil Company, Houston, Tex.

[21] Appl. No.: 797,000

[22] Filed: Nov. 25, 1991

[51] Int. Cl.$^5$ .................................................. C07C 9/52
[52] U.S. Cl. ...................................... 560/205; 554/223
[58] Field of Search .......................... 560/205; 554/223

[56] References Cited

U.S. PATENT DOCUMENTS

| | | | |
|---|---|---|---|
| 2,093,695 | 9/1937 | Larson | 260/106 |
| 3,534,087 | 10/1970 | Leftin et al. | 260/491 |
| 3,641,120 | 2/1972 | Broderick et al. | 260/491 |
| 3,755,386 | 8/1973 | Wilke et al. | 260/410.9 R |
| 3,783,136 | 1/1974 | Inukai et al. | 260/410.9 R |
| 3,855,255 | 12/1974 | Dohr et al. | 260/410.9 R |
| 3,892,788 | 7/1975 | Knifton | 260/410.9 R |
| 4,009,203 | 2/1977 | Schmerlin | 260/497 R |
| 4,144,257 | 3/1979 | Kumobayashi et al. | 260/410.9 R |
| 4,506,095 | 3/1985 | Koermer | 560/205 |
| 4,822,911 | 4/1989 | Fried | 560/205 |

FOREIGN PATENT DOCUMENTS

| | | |
|---|---|---|
| 739208 | 9/1968 | Belgium . |
| 2044159 | 9/1970 | Fed. Rep. of Germany . |
| 3149979 | 12/1980 | Fed. Rep. of Germany . |
| 496265 | 7/1973 | South Africa . |
| 8100846 | 9/1979 | World Int. Prop. O. . |

OTHER PUBLICATIONS

Akermark et al., "Eutectic Potassium-Sodium-Aluminum Chloride as a Mild Catalyst for Ene Reactions: Simple Synthesis of the Sex Pheromone from Douglas Fir Tussock Moth", J. Org. Chem., vol. 43, No. 22, 1978, 4387.

Snider, "The Lewis Acid Catalysis of Ene Reactions", vol. 39, No. 2, 1972, p. 255.

*Primary Examiner*—Paul J. Killos
*Attorney, Agent, or Firm*—Pamela J. McCollough

[57] ABSTRACT

The present invention relates to a process for the preparation of higher alkyl acrylic acid esters which comprises contacting and reacting under ene reaction conditions one or more olefins with one or more alkyl acrylic acid esters in the presense of a catalytically effective amount of an alkoxy aluminum dichloride having a formula R—O—AlCl$_2$, wherein R is alkyl, aryl or a group having a formula R'—C(O)—, wherein R' is alkyl or aryl.

9 Claims, No Drawings

PREPARATION OF CARBOXYLIC ACID ESTERS

FIELD OF THE INVENTION

This invention relates to a process for the preparation of carboxylic acids esters, which are known to find use, for example, in formulating medicines, ointments, cosmetics and lubricating oils, as soaps, as plasticizers, as solvents, and as chemical intermediates. More particularly, this invention relates to a reaction process for the preparation of higher alkyl acrylic acid esters, in which olefins are contacted and reacted with lower alkyl acrylic acid esters, in the presence of an alkoxy aluminum dichloride catalyst.

BACKGROUND OF THE INVENTION

Various catalysts are known to promote the "ene reaction" of olefins with alpha-, beta-unsaturated carboxylic acid esters for the production of unsaturated carboxylic acid esters. For instance, U.S. Pat. No. 3,783,136 and German Offenlengungsschrift both describe the use of $AlCl_3$ and $AlB_3$ as catalysts for such reactions. U.S. Pat. No. 4,506,095 describes the reaction of linear alpha-olefins with alkyl acrylates catalyzed by an organometallic catalyst of the formula $R_n$—Al—$X_{3-n}$, wherein R is an organic radical containing between about 1 and 12 carbon atoms, n is the integer 1 or 2, and X is chlorine or bromine. U.S. Pat. No. 3,641,120 describes the reaction of an ester with an olefin in the presence of a combination of a manganic carboxylic acid salt or oxide with a zirconyl carboxylic acid salt or zirconium oxide. The publication by B. R. Snider on J. Org. Chem., vol. 39, no. 2 (1972), p. 255, refers generally to Lewis acid catalysts for ene reactions, but illustrates only the use of aluminum chloride and zinc bromide. U.S. Pat. No. 3,855,255 describes the reaction of carboxylic acid esters by reacting diolefins with methacrylate esters in the presence of an organometallic complex of zero-valent nickel and an electron donor. U.S. Pat. No. 2,093,695 discloses preparation of carboxylic acid esters by reaction of acyloxy compounds with olefinic hydrocarbons catalyzed by activated charcoal, inorganic acids, the halogens and various halides of calcium, boron, cadmium, zinc, calcium and potassium. Co-pending Application Ser. No. 510,309, filed. Apr. 17, 1990, U.S. Pat. No. 5,066,829 described an ene reaction catalyzed by tantalum pentachoride. Akermark et al (J. Org. Chem., vol. 43, no. 22 (1978), p. 4387) have reported that the eutectic mixture of $AlCl_3$, $NaCl$, and $KCl$ is a superior ene reaction catalyst. U.S. Pat. No. 3,892,788 teaches a ligand-stabilized Pt(II) dihalide complex combined with a Group IVB metal halide as a catalyst for such ene reactions. South African Patent 496,265 describes one such reaction catalyzed by various organo-metal compounds. According to German Offenlegungschrift 2044159, a reaction between acrylic acid esters and dienes is catalyzed by an organometalic complex of zero-valent iron and a triaryl compound of an element of Group V. U.S. Pat. Nos. 3,755,386 and 4,144,257 and Belgian published application 739,208 describe similar reactions using complexes of Group VIII compounds, as well as various compounds and complexes of iron, nickel and cobalt. U.S. Pat. Nos. 4,009,203 and 3,534,087, German Offenlegungsschrift 3149979 and World Pat. No. 8100846 describe related reactions of acids and olefins catalyzed by and acyloxy-stannic trihalide or a perfluorosulfonic acid resin or a crystalline metal silicate or an aluminum silicate containing a Group VIII metal compound and a polyvalent metal halide.

It has been found that alkoxy aluminum dichloride catalysts are very useful in the reaction of alkyl esters of acrylic acid with olefins. Alkoxy aluminum chloride catalysts yield excellent results and are much more convenient to handle than conventional ene reaction catalysts such as ethyl aluminum dichloride because they are not pyrophoric.

SUMMARY OF THE INVENTION

The present invention relates to the reaction of alkyl esters of acrylic acid with olefins promoted by a catalyst comprising a catalytically effective amount of an alkoxy aluminum dichloride having a formula R—O—$AlCl_2$, wherein R is alkyl, aryl or a group having a formula R'—C(O)—, wherein R' is alkyl or aryl.

DESCRIPTION OF THE PREFERRED EMBODIMENTS

The process of the present invention is applicable to the reaction of an olefin (formula I) with an alkyl ester of acrylic acid (formula II) for the preparation of a higher alkyl acrylic acid ester compound (formula III), as represented by the following equation:

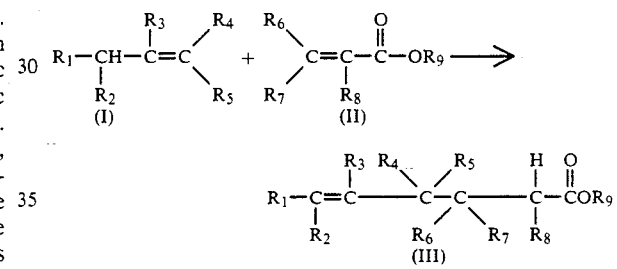

wherein $R_1$ is alkyl, $R_2$, $R_3$, $R_4$, $R_5$, $R_6$, $R_7$ and $R_8$ are each individually selected from the group consisting of hydrogen and alkyl moieties, and $R_9$ is an alkyl group.

The reactant olefins are acylic alkenes, and suitably encompass diolefins, particularly non-conjugated diolefins. In general, the olefin reactant molecule may have from 3 to about 40 carbon atoms. Preferably, the invention is applied to a liquid phase reaction involving olefins in the carbon number range of from about 6 to about 30, inclusive. In one embodiment, preference can be expressed for an olefin reactant carbon number in the range of from about 8 to about 20, inclusive, particularly a carbon number in the range of from about 14 to about 18, inclusive. The olefin molecule is suitably either branched or linear and may have either an alpha- or an internal double bond position. Olefins having a vinylidene structure have been found to be generally more reactive than olefins having a linear structure. More highly branched olefins, produced for example by oligomerization of polypropylene and butylene, are very suitable reactants. Linear internal olefins have generally been observed to have relatively low reactivity and to generate substantial amounts of side products.

Mixed olefin reactants are also very suitable. However, as recognized in U.S. Pat. No. 4,822,911, olefins of different molecular structure may have different reactivities under certain process conditions. Linear olefins having an internal double bond position have also been observed to react more slowly than olefins of other structures and to form substantial amounts of side products.

The lower alkyl esters of acrylic acid which are employed as reactants in this invention are suitably acrylates and alkyl-substituted acrylates represented by formula II above. Mixtures of different alkyl acrylic acid esters are suitable reactants.

The $R_9$ substituent of the ester reactant molecule is preferably an alkyl group having a carbon number of up to about 30, more preferably one having from 1 to about 15 carbon atoms, and most preferably one having from 1 to about 8 carbon atoms. The $R_6$, $R_7$ and $R_8$ substituents each independently represent either a hydrogen atom or an alkyl group, preferably a hydrogen atom or a lower, i.e., $C_1$ to $C_4$, alkyl group. If desired, the acrylate ester reactant may be suitably substituted with one or more non-hydrocarbyl substituents which do not substantially affect the intended reaction. As an example, one or more of the $R_6$, $R_7$ and $R_8$ substituents is suitably a halogen or a halogen substituted alkyl group.

Specific examples of alkyl acrylic acid ester reactants include methyl acrylate, ethyl acrylate, n-propyl acrylate, isopropyl acrylate, n-butyl acrylate, isobutyl acrylate, tertiary butyl acrylate, n-octylacrylate, isooctyl acrylate, 2-ethylhexyl acrylate, n-tetradecyl acrylate, n-hexadecyl acrylate and methyl alpha-chloroacrylate. In one respect, alkyl acrylic acid esters having from 4 to about 8 total carbon atoms are particularly preferred ester reactants. In another respect, preference can be expressed for ester reactants in which the $R_6$, $R_7$ and $R_8$ substituents are each hydrogen. Very good results have been obtained with methyl acrylate.

Also suitable as alkyl acrylic acid ester reactants in the process of the present invention are the dimers, trimers, and other oligomers of the indicated acrylic acid esters, such as, for example, trimethylolpropane triacrylate, 1,6-hexanediol diacrylate, and the like.

The relative proportions of the olefin reactant and the ester reactant are not critical to the invention. However, preference can be expressed for a molar ratio of olefin to ester reactant in the range of from about 1:30 to about 10:1. A molar ratio of olefin to ester in the range of from about 1:10 to about 10:1 is considered more preferred, and a ratio in the range of from about 1:4 to about 4:1 is considered most preferred in order to obtain good conversion to the desired product, while minimizing formation of side products.

For purposes of the process of this invention, the olefin reactant and the alkyl acrylic acid ester reactant are contacted, in the liquid phase, in the presence of a catalytically effective amount of an alkoxy aluminum dichloride having a formula $R—O—AlCl_2$, wherein R is alkyl or a group having a formula $R'—C(O)—$, wherein R' is alkyl. Suitable alkoxy aluminum dichloride compounds include acetoxyaluminum dichloride, ethoxyaluminum dichloride, methoxyaluminum dichloride and the like. In a preferred embodiment, the alkoxy aluminum dichloride is selected from the group consisting of acetoxyaluminum dichloride, ethoxyaluminum dichloride and mixtures thereof. The contact and reaction may take place in either a batch or continuous mode.

The catalyst is suitably present in solution in the reaction mixture in a catalytically effective amount, typically at least about 5 percent by mole (% m), based on moles of the olefin reactant. Catalyst quantities in the range of from about 0.1 percent by mole to about 20 percent by mole are generally preferred, while quantities of catalyst in the range of from about 5 percent by mole to about 10 percent by mole are considered most preferred. Substantially greater quantities of catalyst, e.g., up to about 30 percent by mole or more, can be used if desired. As a general rule, the catalyst is soluble, at least in part, in the reaction mixture.

In addition to the reaction and catalyst, it has been found that while not critical, it is useful to add to the reaction mixture a small quantity of an antioxidant material such as hydroquinone, in order to inhibit free-radical initiated polymerization reactions involving the acrylate esters. The alkoxy aluminum dichloride catalyst can be further applied in combination with other ene reaction catalysts, e.g., other halide compounds.

The present invention primarily relates to the use of the alkoxy aluminum dichloride catalyst. In general, the process can otherwise be practiced under conditions characteristic of other ene reaction processes, although certain preferences can be expressed. Thus, the process is suitably carried out at a temperature in the range of from about 0° C. to about 300° C., preferably in the range of from about 40° C. to about 220° C, more preferably in the range of from about 60° C. to about 150° C., and most preferably in the range of from about 80° C. to about 120° C. Pressure is not a critical variable in the process of the invention, although it is desirable that the pressure be sufficient to maintain the olefin and ester reactants substantially in the liquid phase. Operation at pressures between about 0 psig and about 1000 psig are very suitable, although higher pressures, e.g., 2000 psig or greater, are also suitable. If desired, the process can be carried out using a lower carbon number olefin reactant predominantly in the vapor phase under process conditions, and a liquid phase ester reactant.

The process of the invention can be practiced in the presence of a reaction solvent such as, for example, benzene, toluene, hexane, carbon tetrachloride, ethylene chloride, ethyl acetate or other solvents recognized in the art for use in ene reactions. Solvents often enhance the reaction rate, however, solvents are not necessary for the reaction to proceed.

The contact/reaction step converts the reactants, in whole or in part, to higher alkyl acrylic acid ester adducts of the olefins. The product comprises the higher alkyl acrylic acid ester adducts of the olefins represented by formula III above, as well as other higher alkyl acrylic acid ester adduct isomers. Adducts of two or more ester molecules and one olefin molecule may also be produced, particularly when the process is practiced with an excess of ester reactant. Ene reactions of olefins with acrylate esters are known to produce side products including diesters, dimers, and products from catalyst decomposition.

The present invention is, in one respect, useful for the addition of alkyl acrylic acid esters to branched olefin molecules. In this respect, the invention can be applied to the reaction of highly branched olefin mixtures such as propylene and butylene trimers, tetramers and pentamers, and other products of the oligomerization of lower olefins.

The reaction may be terminated by depletion of one or both of the reactants, or upon cooling of the reaction mixture, e.g., to a temperature of about 0° C., depending on the reactivity of the starting olefin. Either during or following termination of the reaction, the product mixture is preferably treated for separation, e.g., by filtration, of catalyst and/or catalyst residues. Generally the catalyst is at least partially soluble in the reaction mixture. To extract catalyst and catalyst residues from solution, it has been found that it is useful to wash the reaction mixture with an aqueous acid solution, e.g., with an equal volume of a 1 to 10 percent by weight aqueous sulfuric acid solution. This extraction technique is further described in the commonly-assigned copending application, Ser. No. 7/510,311, filed Apr. 17, 1990, the disclosure of which is incorporated herein by this reference.

Separation of the higher alkyl acrylic acid ester products from unreacted olefin and/or ester starting materials can be accomplished by distillation or by other procedures known in the art for the processing of ene reaction products.

This invention is particularly useful when applied in connection with the process described in U.S. Pat. No. 4,822,911. For purposes of that process, a mixture of higher carbon number linear olefins and ethyl- and higher alkyl-branched vinylidene olefins is contacted with one or more alkyl esters of acrylic acid in the presence of an ene reaction catalyst, to accomplish, via selective reaction of the vinylidene olefins, both a separation of vinylidene olefins from the linear olefins and a conversion of the alkyl acrylic acid esters. The teachings of the process of U.S. Pat. No. 4,822,911 are incorporated herein by this reference.

The process of the invention is further described with reference to the following examples, which are intended to be illustrative of certain embodiments of the invention without limiting the invention's broader scope. Illustrative Embodiments

ILLUSTRATIVE EMBODIMENTS

Catalyst Preparation

Catalyst Solution A (ethoxyaluminum dichloride)

Under a nitrogen atmosphere, 0.44 grams (0.0095 moles) of dry absolute ethanol was added to 10 milliliters of dry isooctane. To this solution, 4.82 grams of a 25% solution of ethylaluminum dichloride (0.01 moles) in hexane was added dropwise via an addition funnel. Upon addition of the ethylaluminum dichloride, the evolution of gas (ethane) from the solution was observed. The resulting solution, designated "Catalyst Solution A", was then used as indicated in Example 1.

Catalyst Solution B (acetoxyaluminum dichloride)

This catalyst solution was prepared as above except that 8.46 grams (0.017 moles) of a 25% solution of ethylaluminum dichloride in hexane was added dropwise via an addition funnel to 1.0 grams (0.018 moles) of acetic acid in 10 milliliters of isooctane. The resulting solution, designated "Catalyst Solution B", was used as indicated in Example 2.

EXAMPLE 1

A process according to the invention was carried out for the reaction of methyl acrylate with a $C_{12}$-$C_{18}$ olefin reactant (propylene pentamer) having a branched carbon structure. For this purpose, 20 grams of the olefin mixture were contacted with 8.2 grams of methyl acrylate stabilized with hydroquinone in a 100 milliliter autoclave under a nitrogen atmosphere. Catalyst Solution "A" consisting of ethoxyaluminum dichloride was then added and with autoclave was then charged with 100 psi $N_2$. The reaction was commenced according to the parameters presented in Table I. The results of this experiment are presented in Table II.

EXAMPLE 2

Example 2 was carried out in a manner similar to Example 1 except that Catalyst Solution "B" consisting of acetoxyaluminum dichloride was used as the catalyst. Other parameters for this example, together with the process results, are presented in Tables I and II below.

COMPARATIVE EXAMPLE A

Comparative Example A was carried out in a manner similar to Example 1 except that aluminum isopropoxide was added instead of Catalyst Solution A. Other parameters for this example, together with the process results, are presented in Tables I and II below.

COMPARATIVE EXAMPLE B

Comparative Example B was carried out in a manner similar to Example 1 except that tin tetrachloride was added instead of Catalyst Solution A. Other parameters for this example, together with the process results, are presented in Tables I and II below.

As can be seen in the Tables below, both ethoxyaluminum dichloride and acetoxyaluminum dichloride are active catalysts for this ENE reaction, and are both substantially better than tin tetrachloride. Comparative Example A shows that when the aluminum is trisubstituted with alkoxy groups, very poor results are obtained.

TABLE I

| Example No. | Catalyst: mole percent, basis olefin | Grams olefin: methyl acrylate | Reaction Time (hr) | Reaction Temp. (C.) |
|---|---|---|---|---|
| 1 | Ethoxyaluminum Dichloride: 10% | 20:8.2 | 16 | 100 |
| 2 | Acetoxyaluminum Dichloride: 18% | 20:8.2 | 16 | 100 |
| Comp. A | Aluminum Isopropoxide: 10% | 20:8.2 | 16 | 80 |
| Comp. B | Tin Tetrachloride: 10% | 20:8.2 | 8 | 150 |

TABLE II

| | PRODUCT COMPOSITION (% BY WEIGHT) | | | |
|---|---|---|---|---|
| Example No. | Olefin | 1:1 Adduct | 1:2 Adduct | Olefin Dimer |
| 1 | 70.6 | 26.8 | 2.3 | 0.4 |
| 2 | 76.4 | 21.6 | 1.8 | 0.2 |
| Comp. A | 96.8 | 1.2 | 2.0 | 0.0 |
| Comp. B | 87.8 | 9.6 | 2.7 | None detected |

What is claimed is:

1. A process for the preparation of higher alkyl acrylic acid esters which comprises contacting and reacting under ene reaction conditions one or more olefins with one or more alkyl acrylic acid esters in the presence of a catalytically effective amount of an alkoxyaluminum dichloride having a formula R—O—$AlCl_2$, wherein R is alkyl, aryl or a group having a formula R'—C(O)—, wherein R' is alkyl or aryl.

2. The process of claim 1 wherein said alkoxy aluminum dichloride is selected from the group consisting of acetoxyaluminum dichloride, ethoxyaluminum dichloride, methoxyaluminum dichloride and mixtures thereof.

3. The process of claim 1 wherein said alkoxy aluminum dichloride is selected from the group consisting of acetoxyaluminum dichloride, ethoxyaluminum dichloride, and mixtures thereof.

4. The process of claim 1 wherein the olefins have carbon numbers in the range of from about 6 to about 30, inclusive.

5. The process of claim 4 wherein the reactant alkyl acrylic acid esters have carbon numbers in the range of from about 4 to about 8, inclusive.

6. The process of claim 5 wherein the olefins have carbon numbers in the range of from about 8 to about 20, inclusive.

7. The process of claim 6 wherein the olefins have carbon numbers in the range of from about 14 to about 18, inclusive.

8. The process of claim 1, wherein the contact and reaction take place at a temperature in the range of from about 40° C. to about 220° C. and in the presence of from about 0.1 percent by mole to about 20 percent by mole of an alkoxy aluminum dichloride selected from the group consisting of acetoxyaluminum dichloride, ethoxyaluminum dichloride, methoxyaluminum dichloride and mixtures thereof.

9. The process of claim 1, wherein the contact and reaction take place at a temperature in the range of from about 60° C. to about 150° C. and in the presence of from about 5 percent by mole to about 10 percent by mole of an alkoxy aluminum dichloride selected from the group consisting of acetoxyaluminum dichloride, ethoxyaluminum dichloride, methoxyaluminum dichloride and mixtures thereof.

* * * * *